United States Patent [19]
Corbin et al.

[11] Patent Number: 5,393,509
[45] Date of Patent: Feb. 28, 1995

[54] CRYSTALLINE PHASES OF ALF$_k$(OH)$_{3-k}$ AND HALF$_4$

[75] Inventors: David R. Corbin, West Chester, Pa.; Norman Herron, Newark, Del.; David L. Thorn, West Chester, Pa.

[73] Assignee: E. I. Du Pont de Nemours and Company, Wilmington, Del.

[21] Appl. No.: 126,276

[22] Filed: Sep. 24, 1993

Related U.S. Application Data

[63] Continuation-in-part of Ser. No. 978,644, Nov. 19, 1992, abandoned.

[51] Int. Cl.$^6$ .............................................. C01F 7/50
[52] U.S. Cl. .................................. 423/465; 423/462; 423/472; 423/495; 423/629; 502/231
[58] Field of Search ............... 423/462, 472, 495, 629, 423/465; 502/231, 502

[56] References Cited

U.S. PATENT DOCUMENTS

| | | | |
|---|---|---|---|
| 3,178,484 | 4/1965 | Christoph et al. | 260/653.4 |
| 3,697,443 | 10/1972 | Shinoda et al. | 502/231 |
| 3,720,722 | 3/1973 | Wada et al. | 502/231 |
| 3,929,415 | 12/1975 | Wada et al. | 502/231 |
| 3,933,619 | 1/1976 | Kozlowski | 208/60 |

OTHER PUBLICATIONS

Cowley, J. M. et al., *J. Amer. Chem. Soc.*, 70, 105–109, 1948.
Fourquet, J. et al., *Eur J. Solid State Inorg. Chem.*, 25, 535–540, 1988.
LeBail, A. et al., *J. Solid State Chem.*, 77, 96–101, 1988.
Knop, O. et al., *Can J. Chem.*, 63, 516–525, 1985.
McCoy, L. et al., *J. Phys. Chem.*, 67, 1086–1087, 1963.
Cyvin, S. et al., *J. Phys. Chem.*, 75(17), 2609–2615, 1971.
Huglen, R. et al., *Z Naturforsch*, 34a, 1118–1129, 1979.
Menz, D. et al., *Z. Anorg. Allg. Chem.*, 551, 231–239, 1987.
Sidorov, L. et al., *Russian J. Phys. Chem.*, 42, 1384–1386, 1968.
Gibaud, A. et al., *J. Phys. C: Solid State Phys.*, 19, 4623–4633, 1986.
Scholtz, G. et al. *Chem. Phys. Lett.*, 156(1), 125–128, 1989.
Shinn, D. et al., *Inorg. Chem.*, 5(11), 1927–1933, 1966.
Kalaichev, Y. et al., *J. Struct. Chem. USSR*, 24 807–810, 1983.
Pirioul, B. et al., *J. Non-Crystalline Solids*, 46, 105–110, 1981.
Gilbert, B. et al., *Applied Spectroscopy*, 44(2), 299–305, 1990.
Christie, K. et al., *J. Fluorine Chem.*, 20 751–757, 1982.
Chandross, R., *Acta Cryst.*, 17, 1477–1478, (1964).
Bentrup, U., *Eur. J. Solid State Inorg. Chem.*, vol. 29, Supplement, pp. 51–61 (1992).
LeBail et al., *J. Solid State Chem.*, vol. 100, pp. 151–159 (1992).

*Primary Examiner*—Gary P. Straub
*Assistant Examiner*—Timothy C. Vanoy

[57] ABSTRACT

New crystalline phases of the fluoroaluminum compound AlF$_k$(OH)$_{3-k}$ and processes for their preparation and conversion to conventional phases, as well as isolation of solid HAlF$_4$ are disclosed.

4 Claims, 3 Drawing Sheets

CRYSTALLINE PHASES OF ALF$_k$(OH)$_{3-k}$ AND HALF$_4$

CROSS REFERENCE TO RELATED APPLICATIONS

This application is a continuation-in-part of U.S. Ser. No. 07/978,644, filed Nov. 19, 1992, now abandoned.

The present invention relates to new crystalline phases of the fluoroaluminum compound AlF$_k$(OH)$_{3-k}$, processes for their preparation, and processes for the preparation of known crystalline phases of AlF$_3$ from the new phases. The present invention also relates to HAlF$_4$ in the solid phase and a process for its preparation.

Fluoroaluminum compounds, particularly AlF$_3$, are important solid-state catalysts for chlorofluorocarbon isomerization and fluorination. AlF$_3$ is known to exist in several crystalline phases referred to as "alpha", "beta", "gamma" and the like HAlF$_4$ has been previously detected in the vapor phase, but not isolated.

Cowley, J. M. and Scott, T. R., J. Am. Chem. Soc., 1948, 70, 105–109 disclose the preparation of and X-ray diffraction studies of AlF$_k$(OH)$_{3-k}$•nH$_2$O having a range of composition of k=1 to 2 and n=0 to 0.375. The unit cell was found to contain sixteen formula groups. The compounds were cubic with space group Fd3m, and a lattice constant of 9.85 to 9.77 Å (0.985 to 0.977 nm). Upon heating, the hydroxyfluorides were reported to decompose directly to aluminum oxide and fluoride. Despite numerous attempts, samples having a cubic Fd3m crystal structure and a F:Al ratio significantly greater than 2:1 could not be obtained, the highest having a ratio of 2.07:1 (page 108, col. 1). Similar studies were disclosed by Fourquet, J. L. et al., Eur. J. Solid State Inorg. Chem., 1988, 25, 535–540.

Existing art for preparing fluoroaluminum catalysts includes pyrolysis of precursors obtained from aqueous solution (usually with added HF), treatment of Al$_2$O$_3$ with HF at elevated temperature, and treatment of AlCl$_3$ with HF or chlorofluorocarbons. From aqueous solution, compounds such as M$^+$AlF$_4$(H$_2$O)$_2^-$, (M$^+$)$_2$AlF$_5$(H$_2$O)$^{-2}$, or (M$^+$)$_3$AlF$_6^{-3}$ have been obtained. When pyrolyzed the aquo compounds lose primarily water, and if the cation M$^+$ is capable of decomposition or has a volatile fluoro compound, HF or MF is also lost. However, traces of oxygen tend to remain behind giving rise to small amounts of hydroxy- or oxy-aluminum species.

It has been established that the crystal phase of fluoroaluminum compounds is important to their catalytic properties. Thus it is desirable to control the crystal phase and the amount of hydroxy- or oxy-aluminum species in order to control use as catalyst. The present invention provides two new crystal phases of AlF$_3$, and methods for their preparation, as well as HAlF$_4$ in a solid phase and a process for its preparation.

SUMMARY OF THE INVENTION

The present invention comprises an eta phase of AlF$_k$(OH)$_{3-k}$ wherein k is 2.2 to about 3. This phase has a space group Fd3m with a unit cell parameter a of 9.55 to 9.75 Å (0.955 to 0.975 nm) at 25° C. The present invention further comprises a theta phase of AlF$_3$ having space group P4/nmm, unit cell parameters a=10.18 Å (1.018 nm) and c=7.17 Å (0.717 nm), and an X-ray diffraction pattern with peaks at 15.14, 17.46, 21.43, 23.17, 26.38, 27.75, and 29.14 degrees (2θ) using X radiation of 1.54 Å (CuKα).

The present invention further comprises processes for the preparation of the eta phase of AlF$_k$(OH)$_{3-k}$ wherein k is 2.9 to about 3 comprising the pyrolysis of HAlF$_4$, the pyrolysis of βAlF$_3$•3H$_2$O, and the pyrolysis of BH+AlF$_4^-$ wherein B is 1,8-bis (dimethylamino)-naphthalene or BH is tetramethylammonium.

The present invention further comprises a process for the preparation of the theta phase of AlF$_3$ comprising the pyrolysis of BH+AlF$_4^-$ wherein B is 1,8-bis (dimethylamino) naphthalene or BH is tetramethylammonium.

The present invention further comprises a process for the preparation of the alpha phase of AlF$_3$ comprising the calcination of the eta phase of AlF$_k$(OH)$_{3-k}$ wherein k is 2.9 to about 3, the theta phase of AlF$_3$, or a mixture thereof.

The present invention further comprises HAlF$_4$ in a solid phase and a process for its preparation by pyrolysis of HD+AlF$_4^-$ wherein D is pyridine or alkyl substituted pyridine.

DETAILED DESCRIPTION OF THE INVENTION

Figure 1A:
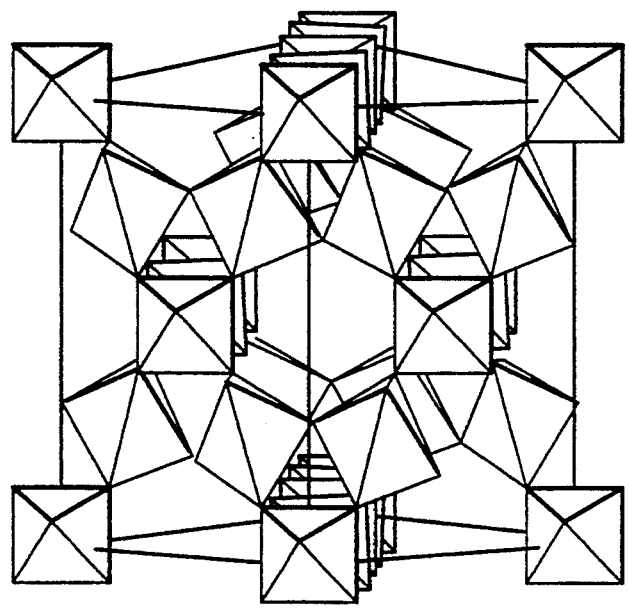
FIGS. 1A and 1B depict the crystalline structure of the eta phase AlF$_k$(OH)$_{3-k}$.

Scheme 1 lists the chemical reactions as equations 1 to 7 for the various processes of the present invention and for the preparation of the compounds of the present invention.

SCHEME 1

$$\text{AlR}^1\text{R}^2\text{R}^3 + 4\text{HF} + \text{D} \longrightarrow \text{R}^1\text{H} + \text{R}^2\text{H} + \text{R}^3\text{H} + \text{H—D}^+\text{AlF}_4^- \qquad \text{(Eqn. 1)}$$

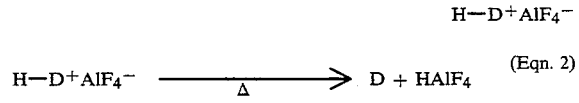

$$\text{H—D}^+\text{AlF}_4^- \xrightarrow[(150°\text{ C.}-285°\text{ C.})]{\Delta} \text{D} + \text{HAlF}_4 \qquad \text{(Eqn. 2)}$$

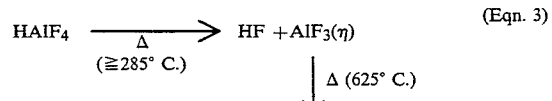
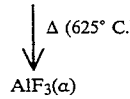

$$\text{HAlF}_4 \xrightarrow[(\geq 285°\text{ C.})]{\Delta} \text{HF} + \text{AlF}_3(\eta) \qquad \text{(Eqn. 3)}$$

$$\xrightarrow{\Delta\ (625°\text{ C.})} \text{AlF}_3(\alpha)$$

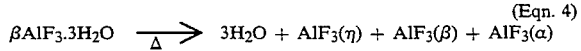

$$\beta\text{AlF}_3\cdot 3\text{H}_2\text{O} \xrightarrow{\Delta} 3\text{H}_2\text{O} + \text{AlF}_3(\eta) + \text{AlF}_3(\beta) + \text{AlF}_3(\alpha) \qquad \text{(Eqn. 4)}$$

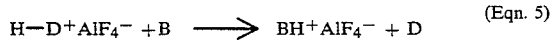

$$\text{H—D}^+\text{AlF}_4^- + \text{B} \longrightarrow \text{BH}^+\text{AlF}_4^- + \text{D} \qquad \text{(Eqn. 5)}$$

-continued
SCHEME 1

$$BH^+AlF_4^-(s) \xrightarrow[(260°\,C.)]{\Delta} BH^+AlF_4^-(liq) \quad \text{(Eqn. 6)}$$

$$\downarrow \Delta\ (>300°\,C.)$$

$$B + HF + AlF_3(\eta) + AlF_3(\theta)$$

$$\downarrow \Delta\ (500°\,C.)$$

$$AlF_3(\alpha)$$

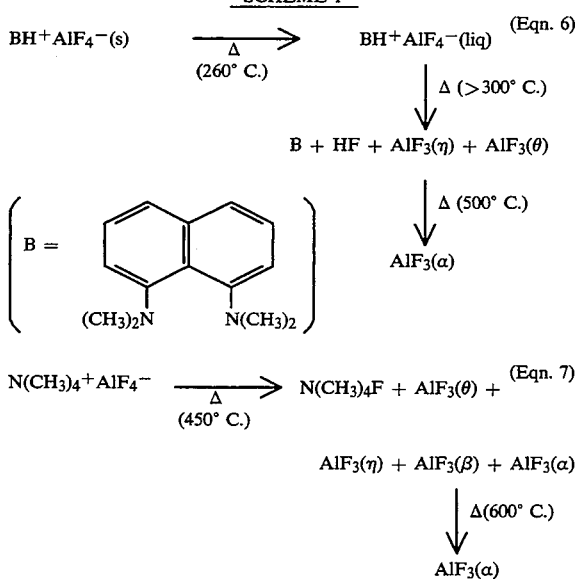

$$N(CH_3)_4{}^+AlF_4{}^- \xrightarrow[(450°\,C.)]{\Delta} N(CH_3)_4F + AlF_3(\theta) + \quad \text{(Eqn. 7)}$$

$$AlF_3(\eta) + AlF_3(\beta) + AlF_3(\alpha)$$

$$\downarrow \Delta(600°\,C.)$$

$$AlF_3(\alpha)$$

The present invention provides a process for the preparation of HAlF$_4$ and its isolation as a solid in accordance with the reaction sequences depicted in equations 1 and 2 in Scheme 1.

In these reactions R$^1$, R$^2$, and R$^3$ are independently C$_1$–C$_{10}$ alkyl, C$_1$–C$_{10}$ alkoxy, or C$_1$–C$_{10}$ enolate. D is pyridine or alkyl substituted pyridine.

The aluminum source is first mixed with reagent D in a mole ratio of from about 1:1 to about 1:500 under an inert atmosphere, and HF added as a solution in reagent D. After stirring, the mixture is left to stand at ambient temperature and the precipitated product isolated by filtration or other equivalent means. The product compound HD$^+$AlF$_4^-$ wherein D is pyridine is not appreciably soluble in nonaqueous solvents at ambient temperature. The product compound HD$^+$AlF$_4^-$ wherein D is pyridine often contains small excess amounts of pyridine, which have no significant effect on its subsequent reactivity.

HD$^+$AlF$_4^-$ is then subjected to pyrolysis in a thermogravimetric analyzer, or other suitable furnace, at a temperature of from about 100° C. to about 285° C., preferably at about 200° C. to about 250° C. A dry inert atmosphere such as nitrogen, argon, or helium is preferably employed. Overall reaction time is from about ½ to about 200 hours, typically from about 1 to about 72 hours. The pyrolysis is conducted at pressures up to 10 atm (1×10$^6$ Pascals), preferably at about 0.1 to 2 atm (1×10$^4$ to 2×10$^5$ Pascals). The resulting HAlF$_4$ is collected as a solid.

When D is pyridine, the pyrolysis reaction proceeds according to equation (2) if the temperature does not exceed 285° C. The compound HAlF$_4$ obtained by this route can also be generated by similar pyrolysis at about 200° C. from the amorphous reaction product of Al(O-isopropyl)$_2$(C$_6$H$_9$O$_3$) and HF-pyridine in a 1:4 ratio. For HAlF$_4$ itself, the pyrolysis reaction proceeds according to equation (3).

HAlF$_4$ is useful as a chemical precursor or intermediate in the preparation of various crystalline phases of AlF$_3$, which are known as solid-state catalysts for chlorofluorocarbon isomerization and for fluorination reactions.

Figure 1B:
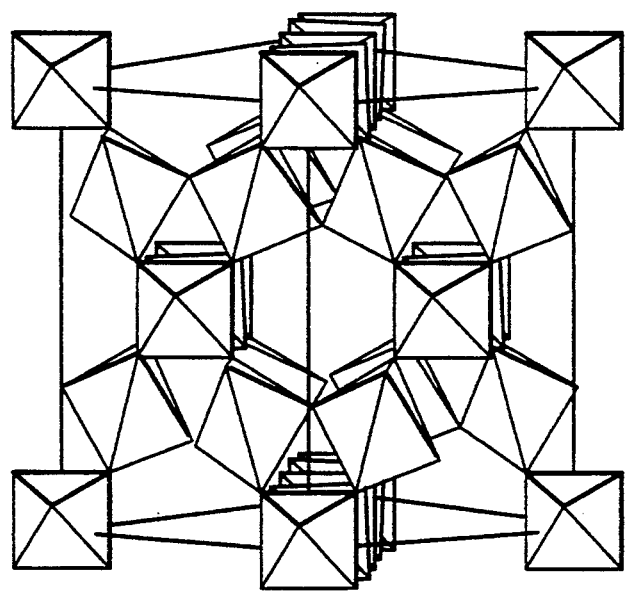

The present invention further comprises a new crystalline phase of AlF$_k$(OH)$_{3-k}$ wherein k is 2.2 to about 3, denoted as the eta ($\eta$) phase. This phase has a space group Fd3m with a unit cell parameter a of from about 9.55 to about 9.75 Å (0.955 to 0.975 nm) at 25° C. Additional details of atomic parameters and selected interatomic distances are provided in Tables III and IV of Example 4, and a polyhedral representation of the structure is shown in FIG. 1. The general structure of the eta phase is that of AlF$_6$ octahedra being corner-linked to form the pyrochlore structure. The tunnel formed by the corner-linked AlF$_6$ octahedra is empty. The eta phase of AlF$_3$ can be viewed as a relative of the established beta-AlF$_3$ phase having similar nanoporous openings defined by corner-shared rings of six [AlF$_6$] octahedra. However, whereas the beta phase material has these openings aligned throughout the crystal to form straight channels along [001], the eta phase has adjacent rings tilted with respect to each other producing an undulating channel along [110] of approximate diameter 2.6 Å (0.26 nm). This undulation is imposed by the other key structural feature of the eta phase—the presence of clusters of four tetrahedrally-disposed [AlF$_6$] octahedra. Three fluoride ions from each of the four octahedra in the cluster are corner-shaped to the other three octahedra of the cluster. The eta phase of AlF$_k$(OH)$_{3-k}$ is useful as a catalyst in fluorination reactions and in chlorofluorocarbon isomerization.

The present invention further comprises processes for the preparation of the eta phase of AlF$_k$(OH$_{3-k}$) wherein k is about 3. One such process comprises the pyrolysis of HAlF$_4$ to generate HF and eta-AlF$_k$(OH)$_{3-k}$ wherein k is about 3 as summarized in equation (3) and the unit cell parameter is a =from about 9.55 to about 9.68 Å (0.955 to 0.968 nm). Such pyrolysis is conducted in an appropriate furnace or thermogravimetric analyzer at a temperature range of from about 285° C. to about 600° C., preferably at about 285° C. to about 400° C. Most preferred is a temperature of from about 300° C. to about 350° C. The pyrolysis is preferably conducted in a dry inert atmosphere such as nitrogen, argon, or helium. A typical reaction time is from about 15 minutes to about 5 hours but can be as long as desired. The reaction is conducted at vacuum to about 100 atm (1×10$^7$ Pascals), preferably at from about 0.1 to about 2 atm (1×10$^4$ to 2×10$^5$ Pascals). The reaction works best if conducted in a flow environment for removal of HF and other volatiles. The desired eta AlF$_k$(OH)$_{3-k}$ is collected as a solid product.

The eta phase of AlF$_k$(OH)$_{3-k}$ wherein k is 2.9 to about 3 and the cell constant is from about 9.55 to about 9.68 Å (0.955 to 0.968 nm) can also be prepared by the pyrolysis of beta AlF$_3$•3H$_2$O according to equation (4). This pyrolysis is conducted at a temperature of from about 100° C. to about 600° C., preferably from about 300° C. to 400° C. Preferably the reaction is conducted in a dry inert atmosphere such as nitrogen, argon, or helium at vacuum to about 10 atm (1×10$^6$ Pascals), preferably at from about 0.1 to about 2 atm (1×10$^4$ to 2×10$^5$ Pascals). The reaction time can range from about 1 to 200 hours, and is typically from about 5 to 72 hours. The desired product is collected as a solid. A better yield of crystalline product is obtained by heating the beta AlF$_3$•3H$_2$O covered in a furnace.

The eta phase of AlF$_k$(OH)$_{3-k}$ wherein k is about 3 can also be prepared by the pyrolysis of BH+AlF$_4^-$ wherein B is 1,8-bis (dimethylamino)naphthalene as discussed below or 2,4,6 trimethylpyridine (collidine).

Figure 2:
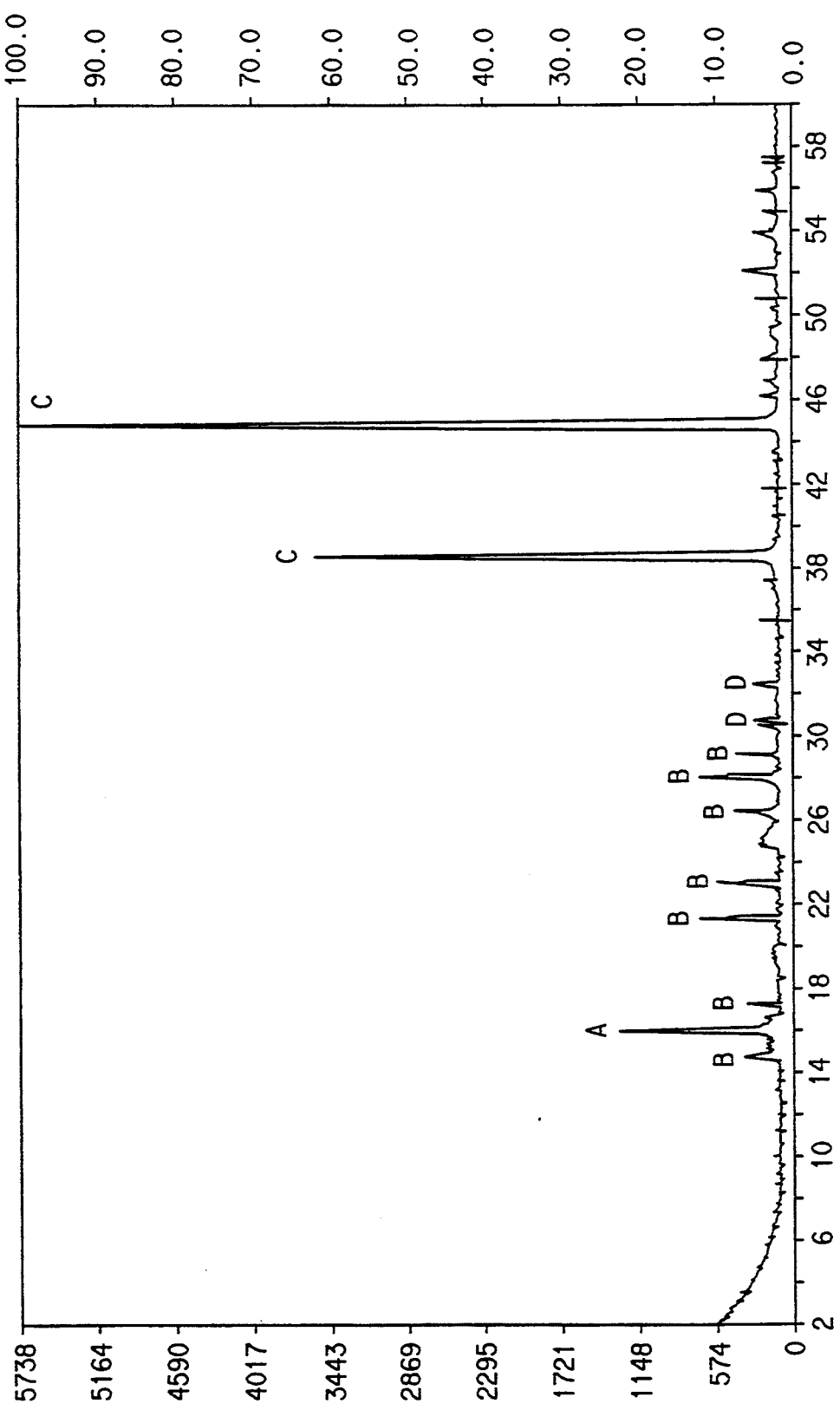
FIG. 2 depicts the powder X-ray diffraction pattern of the eta phase of AlF$_k$(OH)$_{3-k}$ with k of about 3, and the theta phase of AlF$_3$. Those peaks denoted A represent eta AlF$_k$(OH)$_{3-k}$ wherein k is about 3, while those denoted B represent theta AlF$_3$. Those denoted C represent metallic aluminum.
Figure 3B:
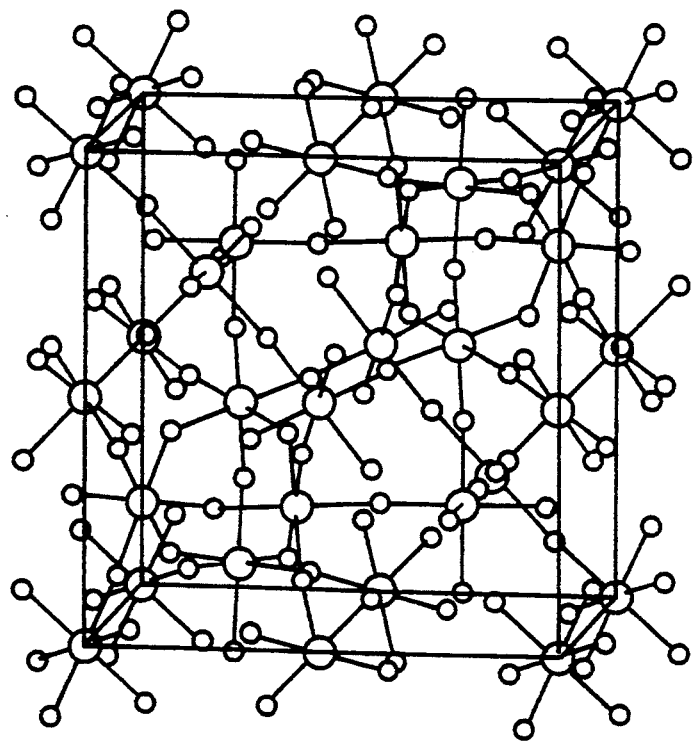
FIGS. 3A and 3B depict the crystalline structure of the theta phase of AlF$_3$.
Figure 3A:
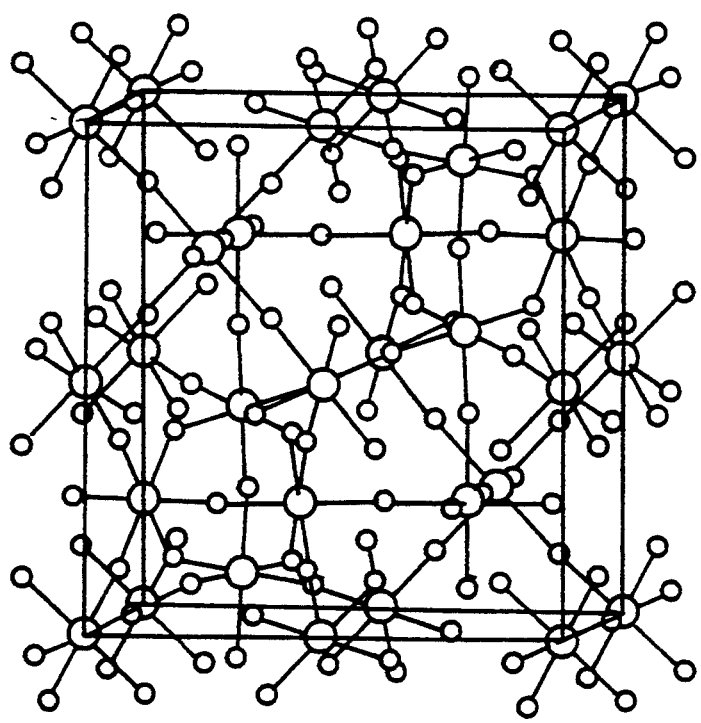

The present invention further comprises a new crystalline phase of $AlF_3$ denoted the theta ($\theta$) phase and a process for its preparation. This compound has an X-ray diffraction pattern with peaks at 15.14, 17.46, 21.43, 23.17, 26.38, 27.75, and 29.14 degrees ($2\theta$) using X radiation of 1.54 Å (0.154 nm) (CuK$\alpha$) as shown in FIG. 2. The corresponding data is listed in Table V of Example 6. The structure of this new phase $\theta$-$AlF_3$ has been elucidated by combined X-ray diffraction and neutron powder diffraction analysis and is shown in FIG. 3. The structure revealed by these techniques is previously unknown for $AlF_3$. This structure again consists of corner-shared $[AlF_6]$ octahedra. The tetragonal unit cell has four independent Al and seven independent F atoms assembled into rings of 5, 4 and 3 $[AlF_6]$ octahedra. The 5-rings (a new structural motif for pure $AlF_3$ phases) form an undulating 3-D interconnected channel system around tetrahedral clusters of four $[AlF_6]$ octahedra—this latter feature being identical to that found in the eta phase above. The microporous nature of this new phase is similar to that of the beta-$AlF_3$ and eta-$AlF_3$ phases—the pores being small, yet still potentially large enough to accommodate small molecules such as HF or $H_2O$ although there is no crystallographic evidence for such inclusions. The theta-$AlF_3$ phase has a space group P4/nmm and a unit cell with cell constants a=10.18 Å (1.018 nm) and c=7.17 Å (.717 nm) at 25° C. Additional details of atomic parameters are provided in Table VI of Example 9, and selected interatomic distances are included in Example 9. The theta phase of $AlF_3$ is useful as a catalyst in chlorofluorocarbon isomerization reactions.

The theta phase of $AlF_3$, as well as the eta phase of $AlF_k(OH)_{3-k}$ wherein k is about 3, are prepared by the pyrolysis of $BH^+AlF_4^-$ wherein B is 1,8-bis (dimethylamino)naphthalene according to equation (6) with substantially no formation of oxides or hydroxide species. The starting material $BH^+AlF_4^-$ can be prepared according to equations (1) and (5). An aluminum source, such as trimethylaluminum, is mixed with reagent D, such as pyridine, under an inert atmosphere and HF added. After stirring, the mixture is left to stand at ambient temperature and the desired $HD^+AlF_4^-$ product precipitates out and can be isolated by filtration or other equivalent means. The $HD^+AlF_4^-$ wherein D is pyridine or alkyl substituted pyridine is then reacted with reagent B wherein B is 1,8-bis (dimethylamino) naphthalene in a mole ratio of 1 or greater according to equation (5) to generate D and H-1, 8-bis (dimethylamino) naphthalene+ $AlF_4^-$ ($BH^+AlF_4^-$). The reaction is conducted at or slightly above room temperature using a pyridine or acetonitrile solvent.

It has been found that it is particularly advantageous to use bases as reagent B in equation (5) such that their conjugate acids $BH^+$ are incapable of forming strong hydrogen bonds to the fluoroaluminate anion, as the resulting compounds $BH^+AlF_4^-$ then tend to be freely soluble in organic solvents. Two particular examples are 1,8-bis(dimethylamino)naphthalene where the conjugate acid, even though possessing NH groups, is a very weak hydrogen-bonding participant; and $(C_2H_5)_3P=CHCH_3$, where the conjugate acid has hydrogen only bonded to carbon and does not normally participate in hydrogen-bonding. Most ylid compounds of phosphorus, arsenic, sulfur, nitrogen, and other elements are suitable to serve as bases B in equation (5) and likewise provide conjugate acid cations $BH^+$ that form only weak hydrogen bonds to fluoroaluminate anions.

A ylid as used herein includes its well known meaning as a compound bearing the group $E=CRR^1$ wherein E is typically N, P, As, or S; and R and $R^1$ are each H, alkyl or aryl groups. The bonding is described as having significant contribution from the resonance form $E^+-C^-RR^1$.

Pyrolysis of $BH^+AlF_4^-$ wherein B is, for example, 1,8-bis (dimethylamino)naphthalene at a temperature of from about 200° C. to about 500° C., preferably at about 300° C. to about 500° C. generates the eta and theta phases of $AlF_3$ plus HF and compound B according to equation (6). The solid H-1,8-bis (dimethylamino) naphthalene+ $AlF_4^-$ is converted to a liquid by heating to about 260° C. providing an $AlF_4^-$-containing molten salt at unprecedented low temperatures. Preferably the pyrolysis is conducted in a dry inert atmosphere such as nitrogen, argon, or helium. Water vapor should be excluded. Reaction time varies from about 15 minutes to 100 hours and is typically about 30 minutes to 2 hours. A pressure from vacuum to 10 atm ($1 \times 10^6$ Pascals) is suitable, and is preferably from about 0.1 to 2 atm ($1 \times 10^4$ to $2 \times 10^5$ Pascals). The eta and theta phases are generated as solids. Preferably the reaction is conducted under an inert gas flow for removal of HF and 1,8-bis (dimethylamino) naphthalene. The compound $(C_2H_5)_4P^+AlF_4^-$ largely volatilizes at about 550° C.

The theta phase of $AlF_3$ can also be prepared by pyrolysis of $N(CH_3)_4^+AlF_4^-$ according to equation (7). Pyrolysis at a temperature of from about 300° C. to 600° C., preferably at about 400° C. to 500° C., generates loss of the equivalent of "$N(CH_3)_4F$" and yields predominantly theta-$AlF_3$, with minor amounts of alpha-$AlF_3$, beta-$AlF_3$ and eta-$AlF_3$. Further heating to about 900° C. results in predominantly alpha-$AlF_3$. Preferably the pyrolysis is conducted in a dry inert atmosphere such as nitrogen, argon or helium with the exclusion of water vapor. Reaction time varies from about 10 minutes to about 120 minutes and is typically about 30 minutes. A pressure of from about $1 \times 10^6$ Pa to about $1 \times 10^4$ Pa is suitable, and is preferably about $2 \times 10^5$ Pa. Use of an inert gas flow to remove volatilized materials is preferred.

The present invention further comprises the preparation of the alpha phase of $AlF_3$ comprising the calcination of the eta phase of $AlF_k(OH)_{3-k}$ wherein k is about 3 and the theta phase of $AlF_3$, or a mixture thereof as shown in equations (3), (6) and (7). The calcination is conducted at a temperature of from about 400° C. to 900° C., preferably at about 500° C. to 750° C. Use of a dry inert atmosphere such as nitrogen, argon, or helium is preferred, with the exclusion of water. The reaction can be run for about 15 minutes to about 100 hours, and typically is conducted for about 30 minutes to 5 hours. A pressure of from vacuum to about 10 atm ($1 \times 10^6$ Pascals) can be employed, preferably from about 0.1 to about 2 atm ($1 \times 10^4$ to $2 \times 10^5$ Pascals). The desired products are collected as solids using conventional isolation techniques.

While the alpha phase is the thermodynamically most stable, the beta, eta and theta phases do not interconvert amongst themselves. There is, therefore, no structural progression through these phases en route to alpha. The phase of $AlF_3$ produced in any given synthesis is apparently dictated by the temperature of synthesis and especially by the precursor from which it is made. In the case of synthesis from organic cation salts of $R^+AlF_4^-$ formulation, a correlation exists between the intermediacy of an $HAlF_4$ material during the thermal decomposition and the phase produced. When the HAlF$_4$ intermediate forms as a discrete phase, eta-AlF$_3$ is invariably produced as the major product, whereas if no such intermediate is formed, theta-AlF$_3$ is the major product.

The various phases of AlF$_3$ are important solid-state catalysts for chlorofluorocarbon isomerization and fluorination reactions. For example, excellent activities for the fluorination of CF$_3$CHCl$_2$ can be obtained using the alpha- and beta-AlF$_3$•3H$_2$O as precursor materials. The eta, beta, and alpha phases of AlF$_3$ are each generated during pyrolysis of these hydrates. In addition to showing improved activities over conventional alumina-based catalysts, these aluminum fluoride hydrates offer the advantage of a simpler activation procedure. The material is activated by simply placing it in the reactor and activating in-situ by heating to about 400° C. in a flowing inert gas such as nitrogen.

EXAMPLE 1 a) Preparation of H-pyridine+AlF$_4$−

Under a N$_2$ atmosphere in a drybox, 0.216 g (3 mmol) trimethylaluminum (CAUTION! This material is pyrophoric in air and reacts vigorously with many solvents, including alcohols, ethers, and pyridine) was dissolved in 20 ml (253 mmol) dry pyridine in a plastic beaker. To this solution was added 0.37 g of HF-pyridine solution (separately determined to have the approximate composition HF (pyridine) 0.135, equivalent weight 30.7) . After the vigorous reaction had subsided, the mixture was stirred for 1 hour. Additional pyridine (20 ml) was added and the mixture was transferred to a glass vessel. After standing 3 days at ambient temperature, the mixture was filtered, and the insolubles dried in vacuum at ambient temperature, yield 0.39 g. The compound H-pyridine+AlF$_4$− prepared in this manner often contains small and variable excess amounts of pyridine, which has no significant effect on its subsequent reactions. Analysis for a representative preparation: Anal. Calcd. for H(pyridine)$_{1.3}$AlF$_4$: C, 37.75%; H, 3.65%; N, 8.80%. Found: C, 37.77, 37.37%; H, 3.57, 3.67%; N, 8.47, 8.69%.

A sample from a second, comparable, preparation was subjected to thermogravimetric analysis and found to have the approximate composition H(pyridine)$_{1.17}$AlF$_4$ assuming the initial weight loss was from the reaction of equation (2) and the second loss, from equation (3).

b) Preparation of HAlF$_4$

A small sample of H-pyridine+AlF$_4$− (~20 mg) was loaded into a Pt sample pan on a Du Pont Instruments 950 thermogravimetric analyzer (TGA). Under a constant flow of dry nitrogen (100 cc/min) the sample was heated from 25° C. to 150° C. at 5° C./min while the weight of the sample was monitored. The weight change observed corresponded well with total loss of pyridine from the original sample composition leaving essentially HAlF$_4$. The sample was then cooled in the flowing nitrogen and a white solid recovered and analyzed for powder X-ray diffraction. The X-ray results are summarized in Table I.

TABLE I

| Peak No. | Angle (deg) | Width (deg) | Peak (cts) | Backg (cts) | D spac (Ang)* | I/Imax (%) | Type A1 | Type A2 |
|---|---|---|---|---|---|---|---|---|
| | | | | HAlF$_4$ | | | | |
| 1 | 8.663 | 0.18 | 5580 | 168 | 10.2080 | 100 | x | x |
| 2 | 13.733 | 0.06 | 55 | 71 | 6.4486 | 1 | x | x |
| 3 | 16.055 | 0.32 | 35 | 66 | 5.5206 | 1 | x | x |
| 4 | 17.345 | 0.18 | 853 | 73 | 5.1128 | 15 | x | x |
| 5 | 18.917 | 0.16 | 61 | 73 | 4.6912 | 1 | x | x |
| 6 | 19.782 | 0.32 | 36 | 73 | 4.4880 | 1 | x | x |
| 7 | 21.175 | 0.24 | 188 | 73 | 4.1959 | 3 | x | x |
| 8 | 22.112 | 0.18 | 1056 | 75 | 4.0201 | 19 | x | x |
| 9 | 23.270 | 0.20 | 350 | 75 | 3.8227 | 6 | x | x |
| 10 | 24.855 | 0.20 | 144 | 75 | 3.5824 | 3 | x | x |
| 11 | 25.555 | 0.12 | 396 | 75 | 3.4858 | 7 | x | x |
| 12 | 28.805 | 0.18 | 620 | 77 | 3.0995 | 11 | x | x |
| 13 | 35.120 | 0.28 | 174 | 50 | 2.5553 | 3 | x | x |
| 14 | 35.682 | 0.16 | 94 | 50 | 2.5163 | 2 | x | x |
| 15 | 37.038 | 0.24 | 35 | 50 | 2.4273 | 1 | x | x |
| 16 | 38.362 | 0.12 | 2411 | 50 | 2.3445 | 43 | x | |
| 17 | 38.452 | 0.10 | 1918 | 50 | 2.3411 | 34 | x | x |
| 18 | 39.438 | 0.32 | 58 | 50 | 2.2849 | 1 | x | x |
| 19 | 42.235 | 0.32 | 77 | 48 | 2.1398 | 1 | x | x |
| 20 | 43.792 | 0.16 | 169 | 48 | 2.0673 | 3 | x | x |
| 21 | 44.605 | 0.14 | 4160 | 48 | 2.0298 | 75 | x | |
| 22 | 44.725 | 0.10 | 3014 | 48 | 2.0297 | 54 | | x |
| 23 | 46.825 | 0.12 | 121 | 48 | 1.9402 | 2 | x | x |
| 24 | 48.097 | 0.32 | 66 | 48 | 1.8918 | 1 | x | x |
| 25 | 50.775 | 0.32 | 71 | 48 | 1.7982 | 1 | x | x |
| 26 | 52.575 | 0.24 | 36 | 47 | 1.7408 | 1 | x | x |
| 27 | 53.850 | 0.40 | 46 | 47 | 1.7025 | 1 | x | x |
| 28 | 57.858 | 0.24 | 128 | 48 | 1.5938 | 2 | x | x |

Generator settings  45 kV, 40 mA
Cu alpha1, 2 wavelengths  1.540598, 1.544435 Ang
Chopper increment, time  0.020 deg, 0.60 s
Peak angle range  2.000–60.000 deg
Peak position criterion  Centroid second derivative
Number of peaks in file  28 (Alpha1: 27, Amorphous: 0)
*1Å = 0.1 nm
(deg) = degree
(cts) = counts
(Ang) = angstroms

EXAMPLE 2

Preparation of H-pyridine+AlF$_4$−

The procedure of Example 1 was carried out except the starting aluminum source was the aluminum alkoxide reagent of formula Al(CH$_3$CHOCH$_3$)$_2$CH$_3$COCHCO$_2$C$_2$H$_5$. 2.743 g of the Al reagent was mixed with 5 mL pyridine in a plastic vial under nitrogen. 1.26 g HF pyridine solution was added very slowly with vigorous stirring. The mixture was stirred for 1 hour and then capped and stored in an oven at 60° C. overnight. The vial was then returned to the nitrogen atmosphere and the cap loosened. The pyridine was allowed to evaporate slowly over 3 days and the white solid was then dried in vacuo to yield the title compound as a poorly crystalline white powder 1.55 g (85%).

EXAMPLE 3

Preparation of H-2,4,6-collidine+AlF$_4$−

100 mg of H-pyridine+AlF$_4$− was slurried into 10 mL 2,4,6-collidine and the mixture was loaded into a tube attached to a vacuum line. The slurry was freeze-/pump/thawed to degas it and then pressured to 700 torr (9.2×10$^4$ Pa) with dry nitrogen gas. The solution was then heated to 200° C. over a period of 30 min. and held there for 1 hour during which time the white solid dissolved. The clear solution was then cooled to room temperature over 45 min. and white needle crystals of the desired product formed on the vessel walls. The crystals were recovered by filtration under a nitrogen atmosphere and identified as the material of the title by X-ray diffraction coupled with thermogravimetric analysis.

EXAMPLE 4

Preparation of eta-AlF$_3$

An identical experimental procedure as in Example 1b) was conducted, but with continued heating of the HAlF$_4$ to 320° C. in the TGA, led to a further weight loss from the sample corresponding to evolution of one equivalent of HF at ~300° C. The evolved HF was identified by gas phase IR. The recovered white solid had a weight corresponding to the stoichiometry "AlF$_3$" and had the X-ray powder data shown in Table II. This powder pattern was similar to that reported by Cowley, J. M., et al., J. Am Chem. Soc., 70, 105–109 (1948) for AlF$_k$(OH)$_{3-k}$ but had smaller cell constants and this new phase has been designated as "eta"-AlF$_3$.

TABLE II eta-AlF$_3$

| Peak No. | Angle (deg) | Width (deg) | Peak (cts) | Backg (cts) | D spac (Ang)* | I/Imax (%) | Type A1 | A2 |
|---|---|---|---|---|---|---|---|---|
| 1 | 8.910 | 0.12 | 21 | 82 | 9.9250 | 0 | x | x |
| 2 | 15.918 | 0.16 | 3697 | 62 | 5.5679 | 64 | x | x |
| 3 | 17.100 | 0.24 | 35 | 62 | 5.1855 | 1 | x | x |
| 4 | 19.677 | 0.56 | 41 | 62 | 4.5117 | 1 | x | x |
| 5 | 21.970 | 0.48 | 64 | 63 | 4.0458 | 1 | x | x |
| 6 | 25.105 | 0.24 | 130 | 63 | 3.5472 | 2 | x | x |
| 7 | 26.160 | 0.14 | 182 | 62 | 3.4065 | 3 | x | x |
| 8 | 29.715 | 0.12 | 28 | 54 | 3.0066 | 0 | x | x |
| 9 | 30.770 | 0.16 | 718 | 50 | 2.9059 | 12 | x | x |
| 10 | 31.625 | 0.06 | 30 | 48 | 2.8292 | 1 | x | x |
| 11 | 32.188 | 0.14 | 615 | 47 | 2.7811 | 11 | x | x |
| 12 | 37.305 | 0.10 | 77 | 31 | 2.4105 | 1 | x | x |
| 13 | 38.325 | 0.10 | 2642 | 34 | 2.3467 | 46 | x | |
| 14 | 38.430 | 0.06 | 2043 | 34 | 2.3425 | 35 | x | x |
| 15 | 40.830 | 0.16 | 59 | 40 | 2.2101 | 1 | x | x |
| 16 | 44.560 | 0.14 | 5776 | 48 | 2.0317 | 100 | x | |
| 17 | 44.700 | 0.06 | 3588 | 48 | 2.0307 | 62 | | x |
| 18 | 46.145 | 0.08 | 433 | 46 | 1.9656 | 8 | x | |
| 19 | 46.298 | 0.08 | 269 | 46 | 1.9643 | 5 | | x |
| 20 | 47.540 | 0.12 | 23 | 43 | 1.9127 | 0 | x | x |
| 21 | 49.120 | 0.10 | 437 | 42 | 1.8533 | 8 | x | |
| 22 | 49.270 | 0.06 | 246 | 40 | 1.8526 | 4 | | x |
| 23 | 51.510 | 0.40 | 18 | 37 | 1.7742 | 0 | x | x |
| 24 | 53.822 | 0.12 | 310 | 33 | 1.7033 | 5 | x | x |
| 25 | 56.513 | 0.14 | 182 | 29 | 1.6285 | 3 | x | x |

Generator settings 45 kV, 40 mA
Cu alpha1, 2 wavelengths 1.540598, 1.544435 Ang
Chopper increment, time 0.020 deg, 0.60 s
Peak angle range 2.000–60.000 deg
Peak position criterion Centroid second derivative
Number of peaks in file 25 (Alpha1: 22, Amorphous: 0)
*1Å = 0.1 nm
(deg) = degree
(cts) = counts
(Ang) = angstroms A bulk sample of this "eta" material was prepared for Rietveld analysis by calcining 2 g of H-pyridine$^+$ AlF$_4^-$ loaded into an alumina boat which was, in turn, loaded inside a quartz-lined horizontal tube-furnace equipped with 100 cc/min nitrogen flow. Heating at 10° C./min to 350° C. with a soak at 350° C. for 1 hour produced ~1 g of white powder having the identical X-ray powder pattern to the above reported TGA sample. This sample provided satisfactory data for subsequent structural refinement of this new phase. The AlF$_3$ powder was compressed into a flat plate and data were collected at the X-7A line of the National Synchrotron Light Source, Brookhaven National Laboratory, Brookhaven, Long Island, N.Y. The beamline was configured in the high resolution mode, using a Si(111) monochromator and Ge(220) analyzer. The wavelength, calibrated using an Si powder standard with a=5.430825 Å (0.5430825 nm) was 0.699392(5) Å (0.0699392(5) nm). Perusal of the X-ray powder diffractogram indicated that all peaks would be explained by either the face centered cubic phase with a=9.62 Å (0.962 nm) for eta-AlF$_3$, or by that of the published data for beta-AlF$_3$. No evidence of lower symmetry was found for the eta-phase.

Structure refinement was initiated using the atomic positions given by Cowley and Scott, J. Am. Chem. Soc., 70, 105–109 (1948) for the hydroxy-analogue of eta-AlF$_3$. Several cycles of least square refinement led to convergence. The final refined parameters are given in Table III. Refinement of the anisotropic model for thermal motion led to an essentially isotropic result and so was not pursued. The final bond distances are reported in Table IV.

TABLE III

Final Parameters for eta-AlF$_3$
Fd3m, a = 9.62247(6)Å, R$_{wp}$ = 0.0968,
R$_p$ = 0.1219, R$_N$ = 0.2311

| Atom | x | y | z | U$_{iso}$ × 10$^2$ (Å$^2$) |
|---|---|---|---|---|
| Al(1) | 0 | 0 | 0 | 2.45(4) |
| F(1) | 0.0620(2) | 7/8 | 7/8 | 2.56(5) |

TABLE IV

Selected interatomic distances and angles for eta-AlF$_3$

| Atoms | Distance (Å)* |
|---|---|
| Al(1)-F(1) × 6 | 1.8026(5) |
| F(1)-F(1) × 4 | 2.5449(22) |
| F(1)-F(1) × 4 | 2.5538(7) |

| Atoms | Angle (°)* |
|---|---|
| Al(1)-F(1)-Al(1) | 141.34(9) |
| F(1)-Al(1)-F(1) × 2 | 179.97(7) |
| F(1)-Al(1)-F(1) × 6 | 89.80(7) |
| F(1)-Al(1)-F(1) × 6 | 90.20(7) |
| F(1)-Al(1)-F(1) × 1 | 180.000(0) |

*number inside parentheses are estimated standard deviations of the least signficiant digit
1Å = 0.1 nm A final difference fourier map did not reveal any density above 1×10$^{-3}$ electrons nm$^{-3}$ (0.001 electrons nm$^{-3}$) at the site expected to be occupied by water in the structure at ($\frac{1}{2}$, $\frac{1}{2}$, $\frac{1}{2}$). As expected for the pure fluoride end member composition of the series Al(OH,F)$_3$, the Al—F and F—F interatomic distances are about 0.04 Å (0.004 nm) shorter than those quoted by Cowley and Scott, J. Am. Chem. Soc., 70, 105–109 (1948). The general features of the structure are as has been described; the AlF$_6$ octahedra being corner-linked to form the pyrochlore structure. Polyhedral representation of the structure of eta-AlF$_3$, viewed down [110] in shown in FIG. 1. The tunnel formed by corner-linked AlF$_6$ octahedra is empty.

EXAMPLE 5

Conversion of eta- to alpha-AlF$_3$

Using the experimental procedure of Example 4, but with continued heating above 320° C. in the TGA after evolution of HF, led to no further weight losses. X-ray diffraction showed a conversion from the eta phase of AlF$_3$ to the known alpha phase of AlF$_3$. No Al$_2$O$_3$ was detected.

EXAMPLE 6

Preparation of theta-AlF$_3$ and eta-AlF$_3$ a) Preparation of BH+AlF$_4^-$, B=1,8-bis(dimethylamino)naphthalene H-pyridine+AlF$_4^-$ (0.19 g) prepared as in Example 1a) and 1,8-bis (dimethylamino) naphthalene (0.21 g) were combined in ca. 2 ml dry acetonitrile, under nitrogen in a drybox. The mixture was stirred and rapidly became a solution. Diethyl ether was then slowly added until precipitation began, at which time the mixture was filtered and the initial precipitate was discarded. More diethyl ether was added to the solution, eventually precipitating 0.19 g white solid, mp 260° C. Anal. Calcd. for C$_{14}$H$_{19}$N$_2$Al$_1$F$_4$: C, 52.83%; H, 6.02%; N, 8.80%; Al, 8.48%; F, 23.88%. Found: C, 52.61, 52.87%; H, 6.06, 5.78%; N, 8.74, 8.80%; Al, 8.73, 8.40%; F, 18.79; 18.70%. The fluoride content was found to be lower than expected, probably due to incomplete decomposition of AlF$_4^-$ during the analytical procedure. IR (Nujol) AlF$_4^-$ at 790 cm$^{-1}$. NMR (0.002M in CD$_3$CN): 19$_F$, −194.2 ppm, 6 lines, J=38 Hz; $^{27}$Al, 51.6 ppm, binomial quintet, J=38 Hz. A single crystal, grown from CH$_2$Cl$_2$/toluene solution, was used for an X-ray structure determination.

b) Preparation of theta-AlF$_3$ and eta-AlF$_3$

A sample from a comparable preparation was analyzed by TGA and found to lose HF and 1,8-bis (dimethylamino)naphthalene at ca. 270°-350° C. The X-ray powder diffraction pattern obtained after heating to 400° C. revealed peaks from the eta phase of AlF$_3$ and peaks from the theta phase of AlF$_3$ as shown in FIG. 2. These data are listed in Table V.

TABLE V

| Peak No. | Angle (deg) | Width (deg) | Peak (cts) | Backg (cts) | D spac (Ang) | I/Imax (%) | Type A1 | Type A2 |
|---|---|---|---|---|---|---|---|---|
| 1 | 15.142 | 0.08 | 266 | 59 | 5.8511 | 5 | x | x |
| 2 | 15.970 | 0.14 | 1156 | 59 | 5.5498 | 21 | x | x |
| 3 | 17.462 | 0.12 | 262 | 57 | 5.0786 | 5 | x | x |
| 4 | 19.755 | 0.64 | 18 | 46 | 4.4942 | 0 | x | x |
| 5 | 21.432 | 0.12 | 610 | 54 | 4.1460 | 11 | x | x |
| 6 | 23.167 | 0.14 | 480 | 50 | 3.8393 | 9 | x | x |
| 7 | 24.737 | 0.16 | 130 | 47 | 3.5991 | 2 | x | x |
| 8 | 26.385 | 0.14 | 299 | 53 | 3.3780 | 6 | x | x |
| 9 | 27.752 | 0.18 | 610 | 51 | 3.2146 | 11 | x | x |
| 10 | 29.140 | 0.12 | 296 | 51 | 3.0646 | 5 | x | x |
| 11 | 30.512 | 0.12 | 79 | 50 | 2.9298 | 1 | x | x |
| 12 | 30.830 | 0.14 | 137 | 50 | 2.9004 | 3 | x | x |
| 13 | 32.233 | 0.14 | 137 | 50 | 2.7773 | 3 | x | x |
| 14 | 35.180 | 0.24 | 10 | 37 | 2.5511 | 0 | x | x |
| 15 | 37.645 | 0.06 | 44 | 32 | 2.3895 | 1 | x | x |
| 16 | 38.400 | 0.12 | 3422 | 40 | 2.3423 | 63 | x |  |
| 17 | 38.495 | 0.08 | 2673 | 40 | 2.3387 | 49 | x | x |
| 18 | 41.818 | 0.32 | 23 | 44 | 2.1602 | 0 | x | x |
| 19 | 44.627 | 0.16 | 5432 | 42 | 2.0288 | 100 | x |  |
| 20 | 44.760 | 0.08 | 3919 | 42 | 2.0282 | 72 |  | x |
| 21 | 46.268 | 0.24 | 117 | 40 | 1.9623 | 2 | x | x |
| 22 | 47.280 | 0.08 | 100 | 39 | 1.9226 | 2 | x | x |
| 23 | 49.143 | 0.08 | 92 | 38 | 1.8540 | 2 | x | x |
| 24 | 50.752 | 0.06 | 56 | 33 | 1.7989 | 1 | x | x |
| 25 | 51.623 | 0.06 | 106 | 33 | 1.7691 | 2 | x |  |
| 26 | 51.790 | 0.12 | 94 | 33 | 1.7653 | 2 | x | x |
| 27 | 52.533 | 0.24 | 164 | 34 | 1.7421 | 3 | x | x |
| 28 | 53.830 | 0.08 | 64 | 33 | 1.7017 | 1 | x |  |
| 29 | 54.030 | 0.06 | 125 | 33 | 1.7001 | 2 |  | x |
| 30 | 54.178 | 0.12 | 110 | 33 | 1.6930 | 2 | x | x |
| 31 | 55.025 | 0.24 | 22 | 32 | 1.6689 | 0 | x | x |
| 32 | 55.770 | 0.06 | 98 | 32 | 1.6484 | 2 | x | x |
| 33 | 56.603 | 0.24 | 28 | 31 | 1.6261 | 1 | x | x |
| 34 | 57.230 | 0.12 | 72 | 31 | 1.6084 | 1 | x |  |
| 35 | 57.425 | 0.08 | 74 | 30 | 1.6047 | 1 | x | x |

| | |
|---|---|
| Generator settings | 45 kV, 40 mA |
| Cu alpha1, 2 wavelengths | 1.540598, 1.544435 Ang |
| Chopper increment, time | 0.020 deg, 0.60 s |
| Peak angle range | 2.000–60.000 deg |
| Peak position criterion | Centroid second derivative |
| Number of peaks in file | 35 (Alpha1: 33, Amorphous: 0) |
| (deg) = degree | |
| (cts) = counts | |
| (Ang) = Angstroms, 1Å = 0.1 nm | |

EXAMPLE 7

Conversion of theta-AlF$_3$ and eta AlF$_3$ to alpha-AlF$_3$

Continued heating of the material of Example 1b) in the TGA to 500° C. converted it to a mixture of eta- and alpha-phases of AlF$_3$, and heating to 750° C. converted it all to alpha-AlF$_3$. Likewise, the material of Example 6b) when heated in the TGA to 500° C. was converted to a mixture of eta- and alpha- phases of AlF$_3$, and heating to 750° C. converted it all to alpha-AlF$_3$.

EXAMPLE 8

Preparation of eta-AlF$_3$

A sample of beta-AlF$_3$•3H$_2$O (Alfa Chemicals) was granulated and then calcined by heating at a rate of 1° C./min to 400° C. and holding at 400° C. for 8 hours. The cooled sample was analyzed by X-ray powder diffraction and determined to contain alpha-AlF$_3$ and a cubic phase resembling AlF$_2$OH.

A sample of the calcined material described above was loaded into a reactor and tested as a catalyst for the fluorination of CF$_3$CHCl$_2$ to CF$_3$CHClF and CF$_3$CHF$_2$. The used catalyst was analyzed by X-ray powder diffraction and determined to contain alpha-AlF$_3$ and a cubic phase resembling AlF$_2$OH.

The unit cell edges of the cubic phase present in the catalysts and other samples generated from the decomposition of beta-AlF$_3$e3H$_2$O were found from X-ray powder diffraction to be smaller than those reported by Cowley and Scott, J. Am. Chem. Soc., 70, 105–109 (1948). By assuming a linear correlation between k in the formula AlF$_k$(OH)$_{3-k}$ and the unit cell edge of the cubic phase based upon the data reported by Cowley and Scott for k of about 1.6 to about 2, and on the data of Exmaple 4 above for k of about 3, the composition AlF$_k$(OH)$_{3-k}$ wherein k is about 2.9 to about 3 can be assigned to the cubic phase present in the above described catalysts and other samples.

EXAMPLE 9

Preparation of theta-AlF$_3$

A sample of the material N(CH$_3$)$_4^+$ AlF$_4^-$ was heated in flowing nitrogen (150 mL/min)at atmospheric pressure (10$^5$ pascal). The temperature was ramped at 10° C./min to 450° C. and held there for 30 minutes. White material sublimed from the bed of N(CH$_3$)$_4^+$ AlF$_4^-$ and the remaining light brown material had a weight corresponding to loss of the equivalent of N(CH$_3$)$_4$F from the original material. The residual powder was theta-AlF$_3$ as shown by its X-ray diffraction pattern and contaminated with very small amounts (<10%) of alpha, beta and eta-AlF$_3$ phases.

The X-ray structural data for theta-AlF$_3$ was collected in a manner similar to that used for the eta phase except that the wavelength used was 0.70059(3) Å

(0.070059 nm), the 2θ range was 5°–60°, the step size was 0.005°, the count time was 4 s, and the sample was both rocked and spun. Although indexing the pattern was quite straightforward yielding a tetragonal unit cell with a=10.1844(1) Å (1.01844 nm) and c=7.1728(1) Å (0.71728 nm), manual deconvolution of the highly overlapped peaks (c≃a/√2, plus the presence of other AlF₃ phases) was found to be necessary in order to correctly assign the intensities from each set of planes. The space group was clearly primitive and an n-glide perpendicular to the unique axis was indicated: space group P4/nmm was thus assigned. Direct methods eventually succeeded in solving the structure but only after some manual intervention in the phasing process. The neutron diffraction data were collected using the HB4 High-Resolution Powder diffractometer at the High Flux Isotope Reactor at Oak Ridge National Laboratory. This instrument has a Ge (115) monochromator; the neutron wavelength was determined to be 1.4163 Å (0.14163 nm) from the Rietveld refinement of nickel and silicon powder standards. Soller-slit collimators of 12 minutes of arc and 20 minutes of arc are positioned before and after the monochromator crystal. A bank of 32 equally spaced (2.7° apart) He-3 detectors, each with a 6 minutes of arc collimator, were step-scanned over a 40 degrees range to provide a diffraction pattern between 11° and 135°. The sample was placed in a vanadium can which was rotated at a rate of 6 rpm during the data collection in order to reduce possible preferred orientation effects. Each intensity in the diffraction pattern was obtained from the average from a number of detectors (this number reaches a maximum of 15 in the central part of the pattern). The intensities shown have been normalized to 3 min/step. The refinement of the structure using both the X-ray and neutron data by the Rietveld method (GSAS) was straightforward although the beta- and eta-AlF₃ phases appeared as minor constituents, 4.7(4) and 4.9(8)% of the sample, and needed to be added to the structure factor calculation as fixed contributors although the scale factors and peak profiles for these contaminant phases were refined. Parameters for the beta-AlF₃ phase were taken from Bail et al., J. Solid State Chem., 77, 96–101 (1988). The unit cell parameters converged at a=10.1844(1) Å (1.01844 nm) and c=7.1728(1) Å (0.71728 nm) in space group P4/nmm. The R values for the X-ray data were: Rwp=0.128, Rp=0.091 and Rn=0.054; for the neutron data: Rwp=0.038, Rp=0.033 and Rn=0.047. The final refined parameters are given in Table VI.

FIG. 3 depicts a stereoview of the theta-AlF₃ structure nearly parallel to the c-axis of its tetragonal cell. The Al-F bond lengths range from 1.738 Å (0.1738 nm) to 1.862 Å (0.1862 nm); the cis and trans F—AL—F angles are all within 3° of 90.0 and 180.0, respectively; and the Al-F-Al angles vary from 140.2° to 180.0°.

TABLE VI

Positional and isotropic thermal parameters for theta-AlF₃

| Atom | X | Y | Z | $U_{iso}$ (Å²)* |
|---|---|---|---|---|
| Al(1) | 0.0 | 0.0 | 0.0 | 0.0071(4) |
| Al(2) | 0.25 | 0.25 | −0.0932(4) | 0.0077(6) |
| Al(3) | 0.25 | 0.25 | 0.4137(4) | 0.0074(7) |
| Al(4) | 0.25 | −0.0862(1) | 0.3274(2) | 0.0070(3) |
| F(1) | 0.1208(1) | 0.1208(1) | −0.0923(3) | 0.0075(5) |
| F(2) | 0.1223(1) | −0.0522(1) | 0.1610(2) | 0.0102(4) |
| F(3) | 0.25 | 0.25 | 0.1573(6) | 0.0119(11) |
| F(4) | 0.25 | 0.25 | −0.3355(6) | 0.0106(11) |
| F(5) | 0.25 | 0.0770(2) | 0.4130(3) | 0.0098(6) |
| F(6) | 0.1262(1) | −0.1262(1) | 0.5 | 0.0111(6) |
| F(7) | 0.25 | −0.25 | 0.2433(5) | 0.0070(8) |

*1 Å = 0.1 nm

What is claimed is:

1. A compound comprising $AlF_k(OH)_{3-k}$ having space group Fd3m wherein k is 2.2 to about 3 having a unit cell parameter a of from about 9.55 to about 9.75 Å (0.955 to 0.975 nm) at 25° C.

2. The compound of claim 1 wherein k is 3 and the unit cell parameter a is from about 9.55 to about 9.68 Å (0.955 to 0.968 nm).

3. A compound comprising AlF₃ having space group P4/nmm and unit cell parameters of a=10.18 Å (1.018 nm) and c=7.17 Å (0.717 nm).

4. A compound comprising HAlF₄ in a solid phase up to about 300° C.

* * * * *